(12) United States Patent
Kinde et al.

(10) Patent No.: US 11,268,132 B2
(45) Date of Patent: Mar. 8, 2022

(54) BARCODED MOLECULAR STANDARDS

(71) Applicant: Thrive Earlier Detection Corp., Cambridge, MA (US)

(72) Inventors: Isaac A. Kinde, Baltimore, MD (US); Howard B. Kaufman, Newton, MA (US); Leonardo Hagmann, Baltimore, MD (US)

(73) Assignee: THRIVE EARLIER DETECTION CORP., Cambridge, MA (US)

( * ) Notice: Subject to any disclaimer, the term of this patent is extended or adjusted under 35 U.S.C. 154(b) by 0 days.

(21) Appl. No.: 16/969,894

(22) PCT Filed: Feb. 14, 2019

(86) PCT No.: PCT/US2019/017973
§ 371 (c)(1),
(2) Date: Aug. 13, 2020

(87) PCT Pub. No.: WO2019/161031
PCT Pub. Date: Aug. 22, 2019

(65) Prior Publication Data
US 2021/0010063 A1    Jan. 14, 2021

Related U.S. Application Data

(60) Provisional application No. 62/631,001, filed on Feb. 15, 2018.

(51) Int. Cl.
*C12Q 1/68* (2018.01)
*C12Q 1/6806* (2018.01)

(52) U.S. Cl.
CPC ................... *C12Q 1/6806* (2013.01)

(58) Field of Classification Search
CPC ....................................................... C12Q 1/68
(Continued)

(56) References Cited

U.S. PATENT DOCUMENTS

2015/0017652 A1    1/2015  Robins
2015/0087535 A1    3/2015  Patel
(Continued)

FOREIGN PATENT DOCUMENTS

WO       2012142213 A2    10/2012
WO    WO-2017165864 A1 *  9/2017  ............. C12Q 1/689
(Continued)

OTHER PUBLICATIONS

Written Opinion of the International Searching Authority for Application PCT/US2019/017973, dated May 17, 2019, 4 pages.
(Continued)

*Primary Examiner* — Aaron A Priest
(74) *Attorney, Agent, or Firm* — Casimir Jones, S.C.; Jason R. Bond (57) ABSTRACT

High throughput personal genomic testing has created a need for robust quality control mechanisms to track sample identity, reagent integrity, and other factors with significant influence on assay performance. A method of massively parallel sequencing using an accompanying barcoded molecular standard enables one to track nucleic acid analytes to identify them by project, lot, batch, or patient. The molecular standard contains sequences present in the analyte, allowing it to be processed simultaneously without any other additional reagents. Within the molecular standard, a calibrator sequence permits assessment of fidelity of sequence determination. Additional sequences in the molecular standard may be used to manipulate the molecular standard separate from the analyte. The molecular standard can be used to benchmark sequencing platforms and assess error rates.

15 Claims, 4 Drawing Sheets

(58) Field of Classification Search
USPC .......................................................... 435/6.1
See application file for complete search history.

(56) References Cited

U.S. PATENT DOCUMENTS

| | | | |
|---|---|---|---|
| 2016/0026758 A1 | 1/2016 | Jabara et al. | |
| 2017/0141793 A1 | 5/2017 | Strauss et al. | |
| 2017/0275691 A1 | 9/2017 | Robins | |
| 2018/0002738 A1 | 1/2018 | Wang et al. | |
| 2018/0237851 A1* | 8/2018 | Christians | C12Q 1/689 |
| 2019/0382837 A1* | 12/2019 | Spurbeck | C12N 15/113 |

FOREIGN PATENT DOCUMENTS

| | | | | |
|---|---|---|---|---|
| WO | WO-2019028462 A1 * | 2/2019 | | C12Q 1/68 |
| WO | WO-2019135790 A1 * | 7/2019 | | G16B 40/30 |

OTHER PUBLICATIONS

Extended EP Search Report for EP19754833.2 dated Jan. 7, 2022, 7 pages.

* cited by examiner

Fig. 1 Calibrator DNA Molecule

Fig. 2 Calibrator DNA Molecule

BARCODED MOLECULAR STANDARDS

BACKGROUND OF THE INVENTION

The workflow encompassing massively parallel sequencing (MPS) of diagnostic testing is fraught with opportunities for processing errors to occur. Errors can occur during sample transport, transfer of samples among multiple containers, processing steps such as library preparation, PCR amplification, sequencing runs, and when reporting results. There is a need in the art for methods and tools that will allow for identification and correction of errors in sample identification, processing steps, and sequencing steps associated with MPS processing.

BRIEF SUMMARY OF THE INVENTION

One aspect of the invention is a method of amplifying a sequencing template in the presence of a calibrator molecule. A plurality of reaction mixtures are formed by mixing together in each reaction mixture: a DNA polymerase; a DNA analyte of a patient sample; a pair of primers complementary to a first and a second strand of the DNA analyte at respective ends of a region to be amplified of the DNA analyte; and a calibrator DNA molecule. The calibrator DNA molecule comprises: two non-contiguous regions which are respectively complementary on opposite strands to the pair of primers; a unique molecular barcode which is unique to a specific patient sample, a specific set of patient samples, a specific project, a specific batch, or a specific lot; and a calibrator region which is distinct from the region to be amplified of the DNA analyte. The unique molecular barcode and the calibrator region are between the two non-contiguous regions. The reaction mixture is incubated under conditions in which the region of the DNA analyte is amplified, forming at least two amplification products. A first amplification product comprises the region of the DNA analyte and a second amplification product comprises the calibrator DNA region. The calibrator DNA molecules in the plurality of reaction mixtures comprise distinct unique molecular barcodes.

Another aspect of the invention is a kit comprising (a) a plurality of calibrator DNA molecules and (b) a pair of primers. The pair of primers is complementary to a first and a second strand of a DNA analyte at respective ends of a region to be amplified of the DNA analyte. The calibrator DNA molecule comprises: two non-contiguous regions which are respectively complementary to the primers on opposite strands; a unique molecular barcode which is unique to a specific patient sample, a specific set of patient samples, a specific project, a specific batch, or a specific lot; and a calibrator region which is distinct from the region of the DNA analyte to be amplified, wherein the unique molecular barcode and the calibrator region are between the two non-contiguous regions. The calibrator DNA molecules in the plurality comprise distinct unique molecular barcodes.

Yet another aspect of the invention is a plurality of sequencing reaction product mixtures. Each sequencing reaction product mixture comprises: an amplified calibrator DNA molecule; and an amplified DNA analyte. The DNA analyte and the calibrator DNA molecule share common 5' and 3' sequences of at least 15 nt. The DNA analyte comprises from 1-200 nt between the common 5' and 3' sequences. The amplified calibrator molecule comprises a unique molecular barcode which is unique a specific patient sample, a specific set of patient samples, a specific project, a specific batch, or a specific lot; and a calibrator region whose sequence is distinct from the 1-200 nt between the common 5' and 3' sequences of the amplified DNA analyte. The unique molecular barcode and the calibrator region are between the common 5' and 3' sequences on the amplified calibrator DNA molecule. The calibrator DNA molecules in the plurality of sequencing reaction product mixtures comprise distinct unique molecular barcodes. The plurality of sequencing reaction product mixtures may be a single project or from a single patient, for example. The plurality of sequencing reaction product mixtures may be contained in a single container, single sequencing apparatus, single laboratory, or single room.

Still another aspect of the invention is a plurality of compositions, each composition comprising (a) a calibrator DNA molecule and (b) a pair of primers. The pair of primers is complementary to a first and a second strand of a DNA analyte at respective ends of a region to be amplified of the DNA analyte. The calibrator DNA molecule comprises: two non-contiguous regions which are respectively complementary to the primers on opposite strands; a unique molecular barcode which is unique to a specific patient sample, a specific set of patient samples, a specific project, a specific batch, or a specific lot; and a calibrator region which is distinct from the region of the DNA analyte to be amplified. The unique molecular barcode and the calibrator region are between the two non-contiguous regions. The calibrator DNA molecules in the plurality of compositions comprise distinct unique molecular barcodes. The plurality of compositions may be contained in a single container, single sequencing apparatus, single laboratory, or single room.

Another aspect of the invention is a plurality of sample collection vessels each of which contains a calibrator DNA molecule to identify a collected sample. The calibrator DNA molecule comprises: two non-contiguous regions of the calibrator DNA molecule which are each complementary to two non-contiguous regions of a region of a DNA analyte in the collected sample; a unique molecular barcode which is unique to a specific patient sample, a specific set of patient samples, a specific project, a specific batch, or a specific lot; and a calibrator region which is distinct from the region of the DNA analyte to be amplified. The unique molecular barcode and the calibrator region are between the two non-contiguous regions. The calibrator DNA molecules in the plurality of vessels comprise distinct unique molecular barcodes. The plurality of sample collection vessels may be contained in a single container, single amplification or sequencing apparatus, single laboratory, or single room.

These and other aspects of the invention which will be apparent to one of skill in the art from the disclosure, provide the art with a simple means to control for many different types of errors which may occur in a scheme of massively parallel sequencing.

DETAILED DESCRIPTION OF THE INVENTION

The inventors have designed a calibrator DNA molecule that can be used for processing with analyte samples in the same vessel. Thus the fate of the calibrator DNA molecule and the analyte are close to identical. The calibrator DNA molecule can be used to assess, for example, amplification errors, purification failures, and sequencing errors. A calibrator DNA molecule may be double stranded or single stranded. It is preferably same length or close to the same length as an analyte amplicon.

The calibrator DNA molecule may be within 10, 100, 250, 500 or 1000 nucleotides of the length of the analyte. In absolute terms it may be, for example, 20-50, 50-200, 200-500, or 500 to 4000 nucleotides in length. The calibrator DNA molecule (overall, or particularly in its calibrator region) may be designed to be similar or distinct in GC content from the analyte. It may have, for example, overall or particularly in its calibrator region, within 5%, 10%, 15%, 25%, 50% or 75% of the GC content of the analyte. In absolute terms, it may have 5%-25%, 25%-45%, 45%-65%, 65%-85%, or 85-95% GC content overall or within its calibrator region.

The unique molecular barcode that forms a part of the calibrator DNA molecule typically will have a distinct sequence from the analyte region to be amplified. The barcodes may be, for example, 2, 3, 4, 5, 6, 7, 8, 9, 10, 15, 20 nucleotides in length. The barcode sequences are not the same as the calibrator region sequences or the DNA analyte sequences, or the same as adjacent sequences to the calibrator region sequences or the DNA analyte sequence. Typically the unique molecular barcodes will vary from one calibrator DNA molecule to another. Thus in a population of calibrator DNA molecules, reaction mixtures, product mixtures, or sample receptacles, the unique molecular barcode is a region of sequence variety that will distinguish one patient sample, project, batch, or lot from another.

DNA polymerases which may be used in the invention are any which are typically used in the course of preparation of samples for massively parallel sequencing. Typically a high fidelity polymerase is desired so that a minimum of unwanted errors are introduced during processing. Amplification that is performed as part of the pre-sequencing processing may be a temperature cycling or isothermal variety.

Any suitable receptacle or vessel for samples, sample preparation, amplification, purification, and sequencing may be used. These may include tubes, wells, vials, microchannels, etc. The material from which the receptacles are made may be any which are employed in the art, including glass, plastic, silicon, metal, etc.

The components of the calibrator DNA molecule can be considered as a linear arrangement of component units. "Between" denotes that a component is before a first element and after a second element in the linear arrangement. "Surrounding" denotes the converse, i.e., that one component occurs before and a second component occurs after the surrounded element. The term "flanking" may be considered as a type of "surrounding," in which the elements are adjacent and abut each other in the linear arrangement.

A kit is a packaged assemblage of elements that can typically be used together. Often the kit will come with or be associated with instructions that provide details on how to use the elements in a process or unified set of processes. Elements in a kit may be separately packaged or be mixed in a single package. Reagents and/or tools and devices may be including, including vessels, measuring devices, reconstituting buffers, enzymes, reaction buffers, lyophilized DNA, etc. Some kits according to the invention may comprise primers and a calibrator DNA molecule. Others components may be included. Some kits may comprise a plurality of sample collection vessels with calibrator DNA molecules pre-allocated to vessels or not.

A calibrator DNA molecule has features which permit a number of useful applications. The unique molecular barcode enables a practitioner to identify individual patients, projects, batches, and/or lots. This feature permits the confirmation of identities when a test report is generated. Primers are complementary to the analyte and to segments or regions of the calibrator DNA molecule permitting co-amplification of the analyte and the calibrator DNA molecule. If the calibrator DNA molecule has not amplified, then proper amplification of the DNA analyte is also not likely to have occurred, since they both employ the same primers. Similarly, if after purification of PCR products, the calibrator DNA molecule is absent, then the purification is unlikely to have been accomplished correctly. The calibrator region of a calibrator DNA molecule can be used to determine error rates. It can provide an assay-specific error rate determination by comparing the input and output calibrator DNA region sequence. Error-prone sequences may be used to increase the sensitivity of error rate determination. The use of calibrator DNA molecules permits dynamic calibration of an assay's limit of detection, assessing inter-platform and inter-laboratory reproducibility, and refining of error rate estimates.

Homopolymeric regions (mononucleotide repeats) in a template or molecular standard or calibrator region may be used to increase the rate of errors of DNA synthesis, for example in amplification or sequencing reactions. Homopolymeric regions of DNA may comprise at least two, at least three, at least four, at least five, or at least 6, 7, 8, 9, 10, 15, or 20 of the same nucleotide in a sequence. Repeated sequences may also be used to increase error rates of DNA synthesis. Repeated sequences are sequences of 2, 3, 4, or 5 nucleotides that are repeated at least 2, 3, 4, or 5 times in tandem. Small tandem repeats and error prone motifs can be used in the calibrator region.

High GC content may also be used to increase the rate of errors of DNA synthesis. A region of a nucleic acid in which guanine and cytosine bases represent over 60%, over 70% over 80%, or over 90% of the nucleotides can be considered to have high GC content. Similarly, methylated CpG motifs may be used to calibrate the error rate of bisulfate sequencing workflows. Alternatively, a calibrator region may be cross-linked or processed with formalin. These can be used, for example, to calibrate DNA damage and/or the fidelity effects of de-crosslinking/fixing protocols. In some embodiments, the calibrator DNA molecules may be added to a tissue or blood sample at the time of sample collection or optionally may be present in a sample collection vessel or device.

DNA samples from blood, serum, plasma, or tissue may be identified with a calibrator DNA molecule upon initial collection and/or receipt, or later after some initial processing. Calibrator DNA molecules may be added to a sample or the sample may be added to the calibrator DNA molecule. The latter can be accomplished when the calibrator DNA molecule is in or is attached to a sample receptacle. Optionally, a calibrator DNA molecule may be in a membrane bound vesicle or other nanoparticle. Breakage or lysis of the vesicle may be used to monitor breakage or lysis of cells in a sample.

DNA may be extracted from a source of cells, if desired according to any method known in the art. Alternatively, the DNA to be analyzed may be cell-free DNA in the blood, serum or plasma. This is sometimes referred to as cfDNA or ctDNA (circulating DNA). Analyte DNA may optionally be prepared for sequencing by attachment of unique identifier sequences (Ms) and universal priming sequences (UPS) in an initial amplification reaction. The resulting amplicons of the initial amplification may be further processed by adding grafting primers and well barcodes. These can be further amplified to increase the number of copies of these DNA templates if desired. A subset of amplified DNA templates may be loaded into a flow cell, which in turn may be loaded into a massively parallel sequencing instrument.

Upon completion of a sequencing run by a massively parallel sequencing instrument, the resulting raw sequencing data may be transferred to a bioinformatics processing workstation. The bioinformatics processing workstation may process the raw sequencing data and output an analysis report of a patient specimen regarding its DNA content and optionally indications of disease.

A unique molecular barcode (UMB) can be designed, fabricated and implemented to be unique to an individual patient, project, batch, or lot. An individual patient sample may be collected from an individual for whom an analytic test is desired. A project may be a systematic investigation that uses one or more samples or reagents to accomplish predetermined objectives. A batch may be a quantity or number of samples or reagents processed at one time or controlled together as a group, often using supplies of the same origin. A lot may be a group of reagents with a common demarcation, source of origin and/or manufactured in the same production run. Individual patient samples, projects, batches or lots desirably should not be misidentified during processing steps. The UMBs provide a mechanism to verify identities. For example, downstream detection of unexpected UMBS can be used as indicators of cross-contamination, and quantitative differential detection of expected UMBs can identify assay failures.

A calibrator DNA molecule can be chosen to yield an assay-specific determination of error rate through the comparison of the input and output calibrator DNA molecule sequence. This method to determine the error rate can also facilitate the dynamic calibration of assay limit of detection and improve cross-laboratory and cross-platform reproducibility (e.g., Illumina MiSeq™ vs. Illumina HiSeq™ vs. Thermo Fisher Ion Torrent™, etc.). The calibrator region may optionally be designed with error-prone sequence motifs (e.g., homopolymer repeats, GC-rich regions, etc.) to refine error-rate calibration in a general or platform-specific manner.

Figure 2:
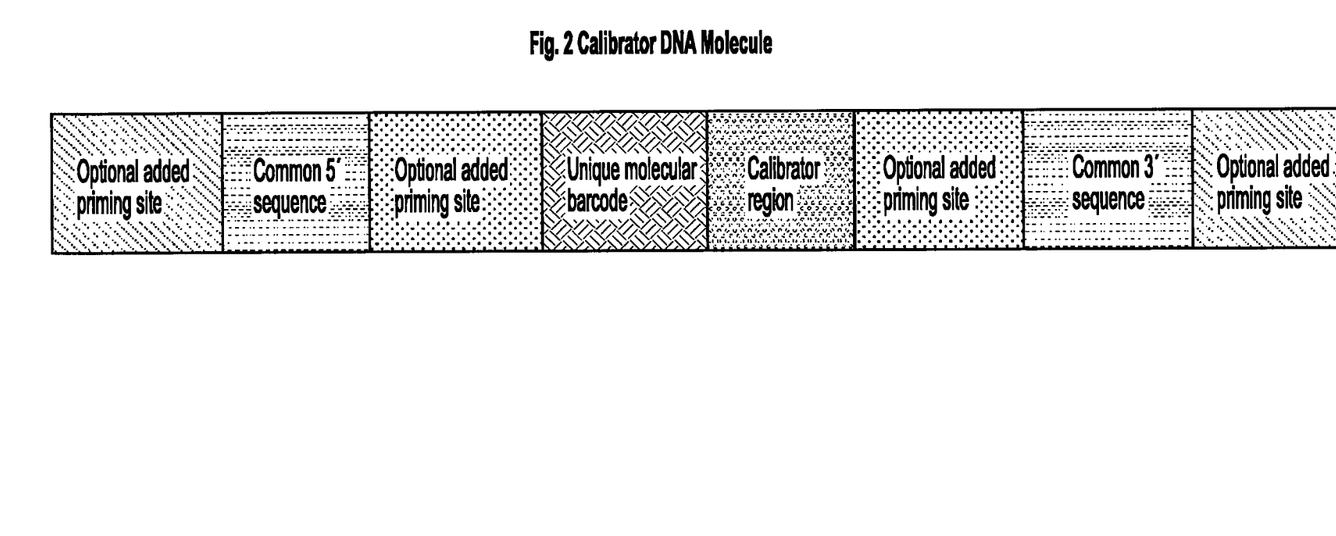
FIG. 2 shows a design for a calibrator DNA molecule with additional features (priming sites) for additional functionality.

Additional optional sequences may be added to a calibrator DNA molecule for additional practical functionality. These sequences may be between the sequences that are complementary to the primers, or they may flank or surround those sequences. These may be used to enable pre- or post-amplification manipulation or detection. See FIG. 2. Sequences flanking the common 5' and 3' sequences can be used for indication of incomplete post-amplification purification. A second, diagnostic amplification can be performed using primers specific to the flanking or surrounding sequences. Optionally, excess barcoded molecular standard can be removed by annealing complementary sequences to the flanking sequence(s), with the complementary sequences immobilized to a solid substrate such as magnetic beads. Optionally the flanking or surrounding sequences may be used as an alternate means to amplify the calibrator DNA molecule as a tool for detecting assay amplification failure.

Figure 1:
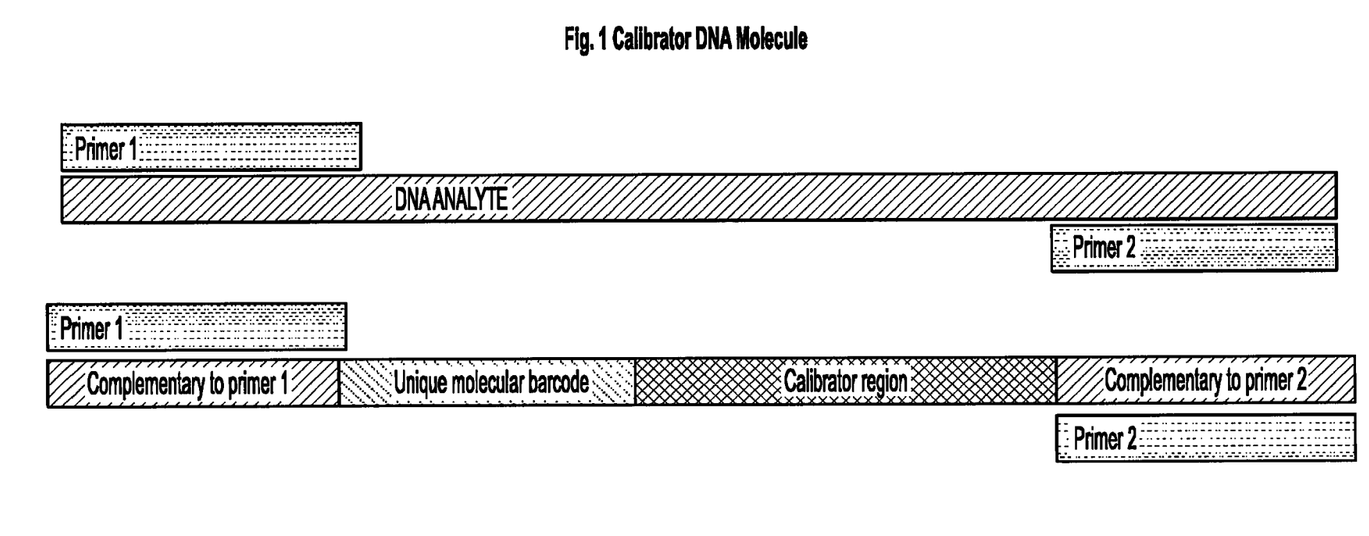
FIG. 1 shows a basic design for a calibrator DNA molecule.

The sequences which are complementary to the primers (FIG. 1) or the common 5' and 3' sequences (FIG. 2) allow the calibrator DNA molecule to be amplified concurrently with a measured analyte genomic DNA from a patient). The calibrator region distinguishes DNA derived from the molecular standard from DNA derived from a sample or analyte). The calibrator region can be non-human, artificial, synthetic, from another species, or derived from a human genomic region not assessed by the assay.

A patient specimen container may have a sample information label affixed to or embedded in a surface of the container. The sample information label may have printed or affixed a unique identifier, for example a standard, 1- or 2-dimensional barcode. A calibrator DNA molecule (containing a molecular barcode) may be included with the patient sample. The calibrator DNA molecule may be added to the patient specimen container before, concurrently, or after the patient sample is added to the patient specimen container. The unique molecular barcode within the calibrator DNA molecule may or may not be correlated with the unique identifier that is on the surface of the container. The correlation can be by means of a table, database, or algorithm to create an identifiable unambiguous correspondence between the calibrator DNA molecule and the unique identifier on the container surface.

The calibrator DNA molecules may be concurrently amplified with DNA fragments originating from the patient specimen, i.e., analyte molecules. The calibrator DNA molecule may be of similar composition and length to a measured analyte (e.g., DNA), such that the sequences of the analyte and calibrator DNA molecule can be amplified and determined simultaneously in a single reaction.

Figure 3:
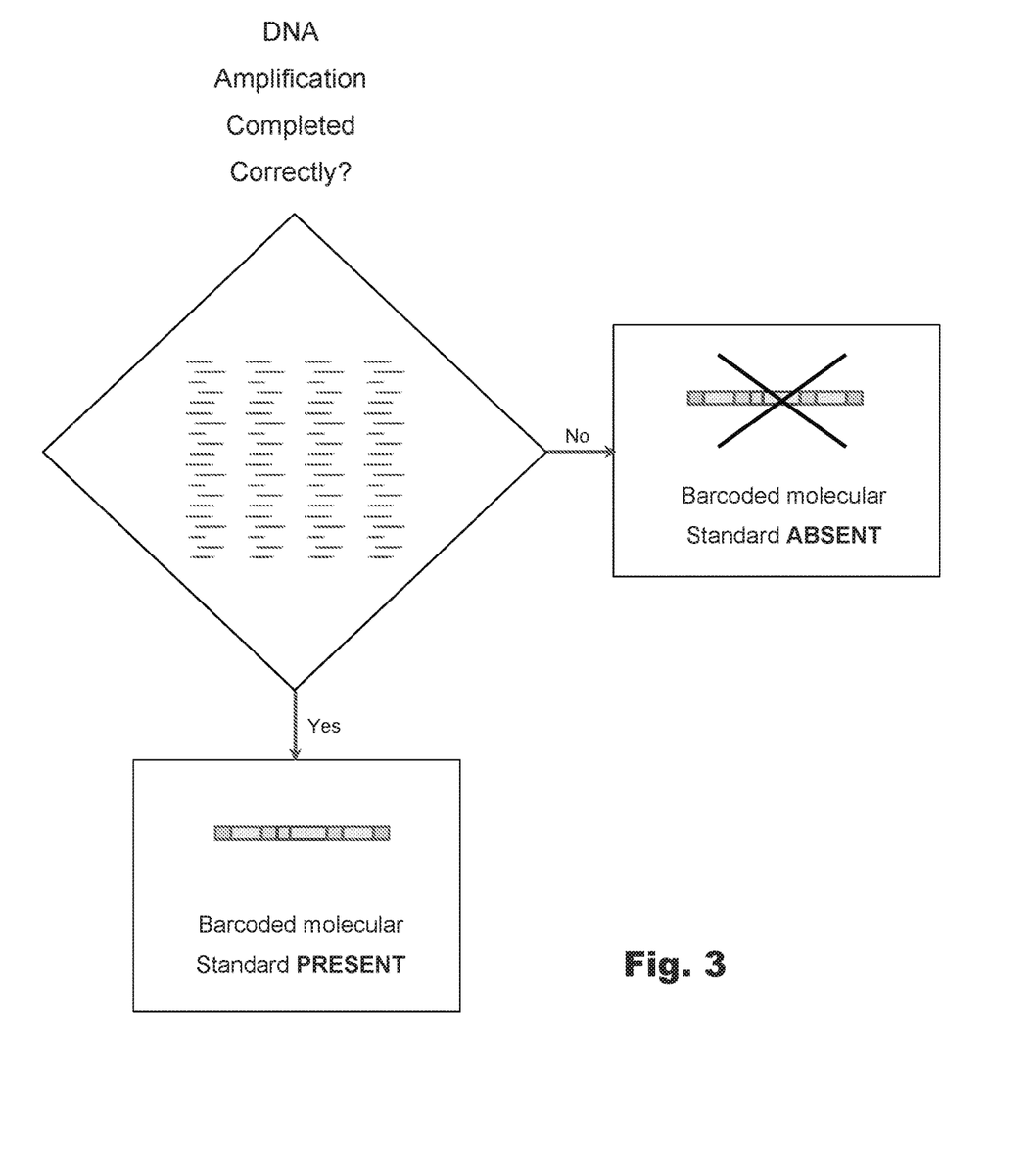
FIG. 3 illustrates how a calibrator DNA molecule permits in-process quality control checking of DNA amplification.

If the calibrator DNA molecule is not detectable after the DNA amplification step, then a processing error has occurred in the massively parallel sequencing workflow at or before the DNA amplification step. See FIG. 3. Alternatively one can check for the presence or absence of the calibrator DNA molecule after a bioinformatics processing workstation has processed the raw sequencing data.

Figure 4:
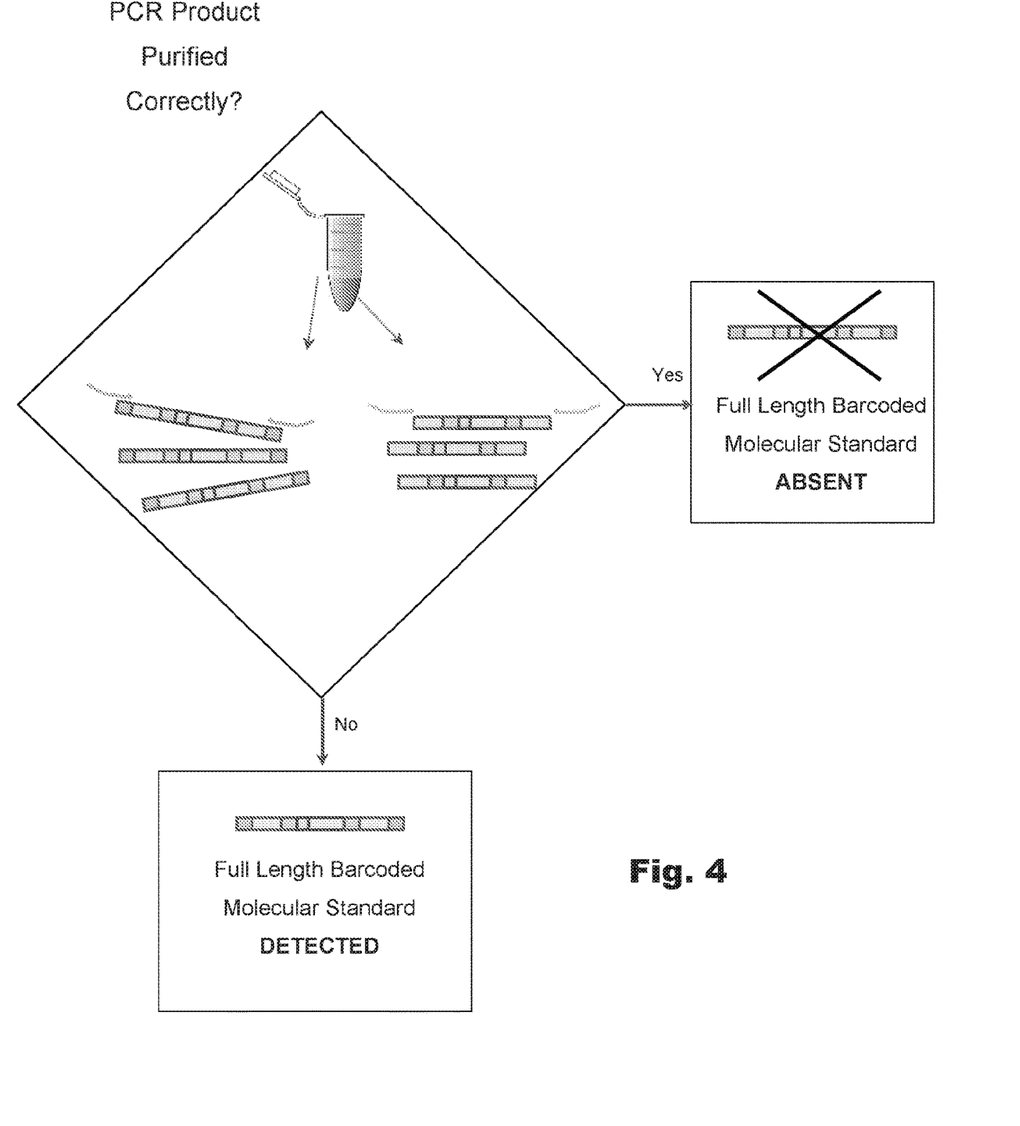
FIG. 4 illustrates how a calibrator DNA molecule permits in-process quality control checking of PCR Purification.

If the calibrator DNA molecule is detectable in its full length after a DNA purification step to separate calibrator DNA molecules from analyte DNA molecules, then a purification of PCR products was incomplete or PCR amplification of the analyte was ineffective. Only the DNA analyte sequences in assay should be detected after amplification and purification. See FIG. 4.

Use of a calibrator DNA molecule has many applications and benefits. The calibrator DNA molecule permits the advantageous determination of error rates and the concurrent identification of individual patients, projects, batches, and/or lots. The determination of error rates in turn enables additional functionality such as the dynamic calibration of assay limit-of-detection, improvement of cross-laboratory and cross-platform reproducibility and refinement of error-rate calibration in a general or platform-specific manner. The identification of individual patients provides confirmation of identities when test reports are generated. Identification of projects, batches, and/or lots is helpful for process troubleshooting and quality control.

A calibrator DNA molecule can be added to a specimen collection medium or device in either its naked form or in an encapsulated form to mimic intact cells (e.g., encapsulated by a hydrophobic membrane, hydrogel, or other nanoparticle technology such as Poly Lactic Acid or Gelatin). These two forms, naked and encapsulated, can be added as a pair to a single sample. This would facilitate assessment of relative amounts of cellular and free nucleic acids.

An RNA calibrator molecule having a similar structure to a DNA calibrator molecule can also be used similarly to the ways of using a DNA calibrator molecule. An RNA calibrator molecule can be used, for example, to monitor RNA sequencing workflows. The calibrator portion may contain, for example, RNA editing motifs so that effects of RNA editing may be quantified. An RNA calibrator molecule and a DNA calibrator molecule may be used in tandem in the same sample. Such samples are typically those which contain an RNA analyte which is subsequently processed by reverse transcription to a DNA form. Use of the two forms, RNA and DNA, permit monitoring of the RNA form of the analyte and its processing. It also permits a comparison of error rates and reverse transcription efficiency and yield. The RNA calibrator molecule may have any and all the features which a DNA calibrator molecule has.

A calibrator DNA molecule may include modified nucleic acid bases to facilitate reduction of molecular contamination. For example, calibrator DNA molecules containing deoxyuridine substituted for deoxythymidine can be efficiently degraded, if desired, i.e., if they are found to be a contaminant. Alternatively, click chemistry or other methodology can be used for the removal of residual primer in purification steps.

A barcoded molecular standard may be added to individual patient samples in a clinical massively parallel sequencing assay at the time of sample acquisition. In the case of samples where the isolation of cell free DNA (cfDNA) is preferred, two distinct calibrator DNA molecules may be added. The first may be, for example, naked nucleic acid in an appropriate buffer. The second may be, for example, encapsulated in a hydrophobic membrane. The two calibrator molecules may have distinct unique molecular barcodes so that they may be distinguished. The sequence identity of each standard is associated with the accessioned sample and may be tracked throughout the assay workflow. If sample handling leads to the lysis of cells and release of genomic DNA, detection of the second standard during sequence analysis may alert the operator.

A barcoded molecular standard can also be added to the extracted and purified analyte immediately prior to amplification in order to more rigorously control specifically for the quality of the steps after amplification.

The non-interfering nature of the barcoded molecular standard permits use of the same manipulative steps as for the massively parallel sequencing assay without the barcoded molecular standard. However, optional steps may be employed. For example, if contamination with molecular standard is suspected and the molecular standard contains 5-(C2-EDTA)-2'-deoxyuridine in its sequence, samples may be treated with, for example, Fe (II) to catalyze specific cleavage of only the contaminating molecular standard.

During analysis of sequencing results, a bioinformatics pipeline may recognize and segregate the sequencing reads representing the barcoded molecular standard from those representing analyte. The levels of barcoded molecular standard detected may be normalized across samples based on input quantities.

If a molecular standard is selected containing an error prone motif, for example, homopolymer repeats such as GGGGCCCCC, prior knowledge of this motif allows for calibration of sequencing equipment between platforms, and on the same platform between runs. For each position in the known error-prone motif, a substituted base specific error rate can be calculated in order to tune variant base-calling algorithms. Alternatively, regions of similar complexity to the assayed nucleic acid amplicons can be used in addition to or instead of the error prone motifs, to benchmark sequencing platform performance in a fashion tailored to the assay in question.

As individual sequencing platforms have previously published sequencing bias and coverage bias, the use of these previously reported bias-inducing motifs allows for the quantitation of the context specific bias in the particular application of the assay in question. While sequencing bias motifs can be used to train variant base-calling algorithms, coverage bias motifs can be used to train relative expression models.

We claim:

1. A method of amplifying a sequencing template in the presence of a calibrator double-stranded DNA molecule, comprising:
   a) forming a plurality of reaction mixtures by mixing together in each reaction mixture:
      a DNA polymerase;
      a DNA analyte of a patient sample;
      a pair of primers complementary to a first and a second strand of the DNA analyte at respective ends of a region to be amplified of the DNA analyte; and
      a calibrator double-stranded DNA molecule comprising:
         two non-contiguous regions which are respectively complementary to said pair of primers, wherein each said two non-contiguous regions is present in different strands of said calibrator double-stranded DNA molecule;
         a unique molecular barcode which is unique to a specific patient sample, a specific set of patient samples, a specific project, a specific batch, or a specific lot; and
         an input calibrator region which is distinct from the region to be amplified of the DNA analyte, wherein the unique molecular barcode and the input calibrator region are between the two non-contiguous regions, and wherein i) the overall GC content of the input calibrator region is over 60%, and/or ii) the input calibrator region comprises a homopolymer repeat that is at least 7 of the same nucleotide in a sequence; and
   b) incubating the reaction mixture under conditions in which the region of the DNA analyte, and the input calibrator region, are amplified, forming at least two amplification products, wherein a first amplification product comprises the region of the DNA analyte and a second amplification product comprises an output calibrator region, wherein the plurality of reaction mixtures comprise calibrator double-stranded DNA molecules with distinct unique molecular barcodes.

2. The method of claim 1 wherein the DNA polymerase is a high fidelity polymerase.

3. The method of claim 1 wherein temperature is cycled during the step of incubating.

4. The method of claim 1 wherein the step of incubating is isothermal.

5. The method of claim 1 wherein the input calibrator region comprises damaged DNA.

6. The method of claim 1, wherein the overall GC content of said input calibrator region is over 70%.

7. The method of claim 1, wherein the input calibrator region comprises a homopolymer repeat that is at least 8 of the same nucleotide in a sequence.

8. The method of claim 1 wherein the input calibrator region is a non-human DNA sequence.

9. The method of claim 1 wherein the calibrator double-stranded DNA molecule and the DNA analyte are pre-mixed.

10. The method of claim 1 wherein the calibrator double-stranded DNA molecule is present in a sample collection vessel when a sample is collected from a patient.

11. The method of claim 1 wherein the calibrator double-stranded DNA molecule comprises a pair of priming sites distal to and surrounding the two non-contiguous regions, wherein said pair of priming sites are not present in the analyte DNA, said pair of priming sites capable of priming amplification of the calibrator double-stranded DNA molecule without priming amplification of the DNA analyte.

12. The method of claim 1 wherein the calibrator double-stranded DNA molecule comprises a pair of priming sites distal to and surrounding the calibrator region and the unique molecular barcode, said pair of priming sites for amplifying the calibrator region and the unique molecular barcode without amplifying the region of the DNA analyte to be amplified.

13. The method of claim 1 wherein the calibrator double-stranded DNA molecule comprises one or more modified nucleotide bases which are not naturally occurring in the DNA analyte.

14. The method of claim 1, wherein the overall GC content of the input calibrator region is over 80%.

15. The method of claim 1, wherein the input calibrator region comprises a homopolymer repeat that is at least 9 of the same nucleotide in a sequence.

\* \* \* \* \*